(12) United States Patent
Toth et al.

(10) Patent No.: US 7,082,183 B2
(45) Date of Patent: Jul. 25, 2006

(54) COMPUTED TOMOGRAPHY DOSE INDEXING PHANTOM SELECTION FOR DOSE REPORTING

(75) Inventors: Thomas Louis Toth, Brookfield, WI (US); David Michael Hoffman, New Berlin, WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 10/710,563

(22) Filed: Jul. 21, 2004

(65) Prior Publication Data
US 2006/0018435 A1   Jan. 26, 2006

(51) Int. Cl.
*H05G 1/28* (2006.01)
(52) U.S. Cl. ............................ 378/16; 378/4
(58) Field of Classification Search ............ 378/4, 378/8, 16, 18, 19, 20, 97, 165, 205, 108, 378/109, 110, 98, 7, 156–159
See application file for complete search history.

(56) References Cited

U.S. PATENT DOCUMENTS

| | | | |
|---|---|---|---|
| 5,400,378 A * | 3/1995 | Toth ............................ 378/16 |
| 6,028,907 A * | 2/2000 | Adler et al. ..................... 378/4 |
| 6,307,918 B1 * | 10/2001 | Toth et al. ................... 378/158 |
| 6,490,337 B1 * | 12/2002 | Nagaoka et al. ............... 378/20 |
| 6,778,628 B1 * | 8/2004 | Yamazaki et al. .............. 378/8 |
| 2003/0016778 A1 * | 1/2003 | Tachizaki et al. .............. 378/4 |
| 2003/0185343 A1 | 10/2003 | Horiuchi |
| 2004/0013223 A1 * | 1/2004 | Yamazaki et al. .............. 378/4 |
| 2004/0086076 A1 * | 5/2004 | Nagaoka et al. ................ 378/4 |
| 2004/0101105 A1 * | 5/2004 | Segawa et al. ............. 378/108 |
| 2004/0131141 A1 * | 7/2004 | Horiuchi ......................... 378/4 |

* cited by examiner

*Primary Examiner*—David V. Bruce
*Assistant Examiner*—Hoon Song
(74) *Attorney, Agent, or Firm*—Pete Vogel, Esq.

(57) ABSTRACT

A computed tomography assembly is providing including an x-ray gantry assembly, an x-ray source projecting a beam of x-rays, a detector assembly positioned opposite the x-ray source and receiving the beam of x-rays, and a control mechanism in communication with the x-ray source and the detector assembly. The control mechanism includes logic adapted to: execute at least one scout scan of the object to produce a first scout scan image; generate an elliptical patient model based on the first scout scan image; match the elliptical patient model to a phantom diameter approximation; generate a dose report based on the phantom diameter approximation; and display said dose report on a display in communication with the control mechanism.

18 Claims, 5 Drawing Sheets

COMPUTED TOMOGRAPHY DOSE INDEXING PHANTOM SELECTION FOR DOSE REPORTING

BACKGROUND OF INVENTION

The present invention relates generally to a computed tomography assembly, and, more particularly to a computed tomography assembly with improved phantom selection for dose reporting.

Computed tomography has been utilized for a wide variety of imaging applications. One such category of applications is comprised of medical imaging. Although it is known that computed tomography may take on a wide variety of configurations within the medical industry, it commonly is based on the transmission of low energy rays through a body structure. These energy rays are subsequently received and processed to formulate an image, often three-dimensional, of the body structure that can by analyzed by clinicians as a diagnostic aid.

The reception of energy rays, such as gamma rays or x-rays, is often accomplished through the use of a device referred to as a detector assembly. The detector assembly is typically comprised of a plurality of structures working in concert to receive and process the incoming energy rays after they have passed through the body structure. The detector assembly utilizes scintillator to absorb the photons and convert their energy into visible light. This allows the energy rays received by the scintillator detector to be converted into useful information. Scintillator elements may come in a wide variety of forms and may be adapted to receive a wide variety of incoming rays. The light produced by the scintillator element is commonly processed by way of a device such as a light sensitive photodiode, which converts the light from the scintillator element into an electronic signal. In this fashion, the information from the scintillator detector can be easily transferred, converted, and processed by electronic modules to facilitate viewing and manipulation by clinicians.

Although CT scans provide a highly useful and critical medical diagnostic element, they must still be recognized to be a tool that, if improperly utilized, may pose concerns to the patients on which it is utilized. The methodology operates through the use of gamma rays and x-rays which are only suitable for human exposure within limits. The human body absorbs radiation during exposure to the CT imaging process. Excessive exposure to such radiation provides additional medical concerns. Patient size, imaging region cross-section, imaging region area all play a role in determining the minimum radiation exposure necessary for clear imaging. Computed Tomography Dose Indexing (CTDI) is a standard dose measurement methodology required to be utilized by all computed tomography manufactures. The methodology utilizes phantoms for reporting typical head and body dosages. New regulations require the CTDIvol to be displayed to the operator after selecting the scan but before executing the scan. Methodologies for determining the CTDIvol commonly utilize assumptions regarding patient size to provide such estimated CTDIvols prior to imaging. Proper phantom size is dependent not only on patient size, but the portion of body to be imaged as well. Rather than rely on operator estimations such as adult/head or child/body, a more accurate and consistent CTDIvol dose reporting would be preferred.

It would, therefore, be highly desirable to have computed tomography assembly with improved CTDIvol reporting reliability. Additionally, it would be highly desirable to have a computed tomography assembly with CTDIvol reporting tailored to the specific patient/imaging portion presently being imaged.

SUMMARY OF INVENTION

A computed tomography assembly is providing including an x-ray gantry assembly, an x-ray source projecting a beam of x-rays, a detector assembly positioned opposite the x-ray source and receiving the beam of x-rays, and a control mechanism in communication with the x-ray source and the detector assembly. The control mechanism includes logic adapted to: execute at least one scout scan of the object to produce a first scout scan image; generate an elliptical patient model based on the first scout scan image; match the elliptical patient model to a phantom diameter approximation; generate a dose report based on the phantom diameter approximation; and display said dose report on a display in communication with the control mechanism.

Other features of the present invention will become apparent when viewed in light of the detailed description of the preferred embodiment when taken in conjunction with the attached drawings and appended claims.

DETAILED DESCRIPTION

Figure 1:
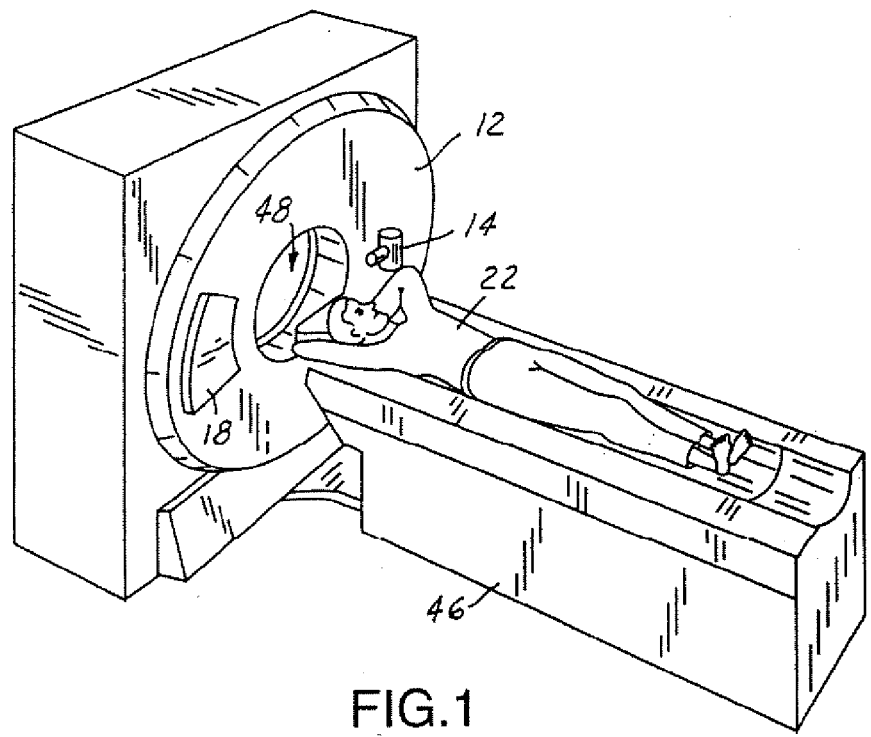
FIG. 1 a computed tomography assembly in accordance with the present invention.
Figure 2:
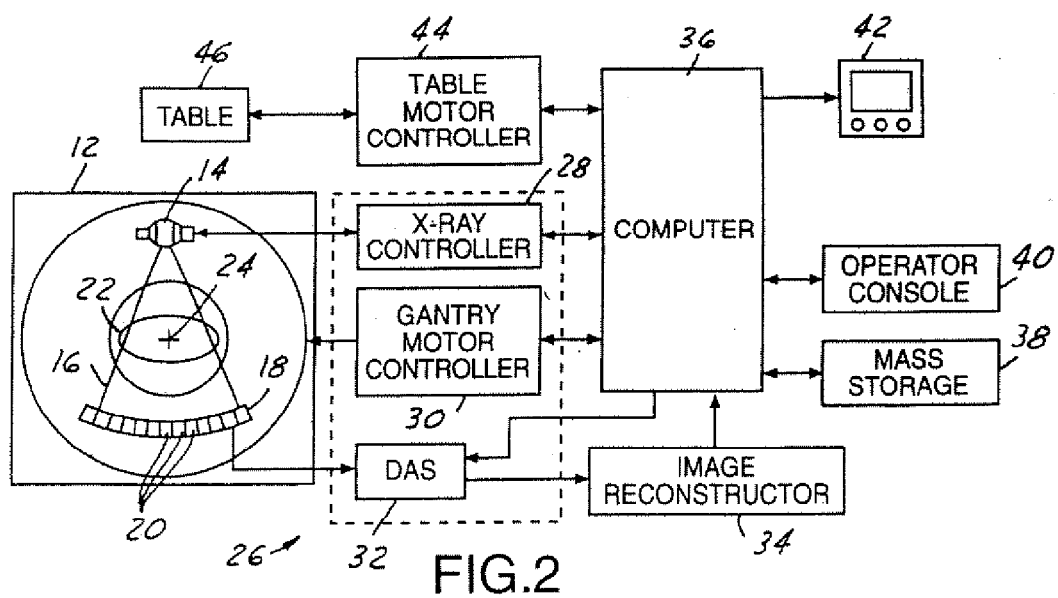
FIG. 2 is a diagram of the computed tomography assembly illustrated in FIG. 1.

Referring now to FIGS. 1 and 2, which are illustrations of a computed tomography (CT) imaging system 10 for use with the detector assembly 18 of the present invention. Although a particular CT imaging system 10 has been illustrated, it should be understood that the detector assembly 18 of the present invention could be utilized in a wide variety of imaging systems. The CT imaging system 10 includes a scanner assembly 12 illustrated as a gantry assembly. The scanner assembly 12 includes an x-ray source 14 for projecting a beam of x-rays 16 toward a detector assembly 18 positioned opposite the x-ray source 14. The detector assembly 18 includes a plurality of detector elements 20, referred to as a detector array, which combine to sense the projected x-rays 16 that pass through an object, such as a medical patient 22. Each of the plurality of detector elements 20 produces an electrical signal that represents the intensity of an impinging x-ray beam and hence the attenuation of the beam 16 as it passes through the object of patient 22. Commonly, during a scan to acquire x-ray projection data, the scanner assembly 12 is rotated about the center of rotation 24. In one embodiment, illustrated in FIG. 2, detector elements 20 are arranged in one row such that projection data corresponding to a single image slice is acquired during a scan. In other embodiments, the detector elements 20 can be arranged in a plurality of parallel rows, such that projection data corresponding to a plurality of parallel slices can be acquired simultaneously during a scan.

The rotation of the scanner assembly 12 and the operation of the x-ray source 14 are preferably governed by a control mechanism 26. The control mechanism 26 preferably includes an x-ray controller 29 that provides power and timing signals to the x-ray source 14 and a scanner motor controller 30 that controls the rotational speed and position of the scanner assembly 12. A data acquisition system (DAS) 32 in control mechanism 26 samples analog data from the detector elements 20, commonly a photodetector array, and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

The computer 36 also can receive commands and scanning parameters from an operator via console 40 that has a keyboard or similar input device. An associated display 42 allows the operator to observe the reconstructed image and other data from the computer 36. The operator supplied commands and parameters are used by computer 36 to provide control signals and information to the DAS 32, x-ray controller 29, and scanner motor controller 30. In addition, the computer 36 operates a table motor controller 44 which controls a motorized table 46 to position patient 22 within the scanner assembly 12. Particularly, the table 46 moves portions of the patient 22 through the scanner opening 48.

Figure 3:
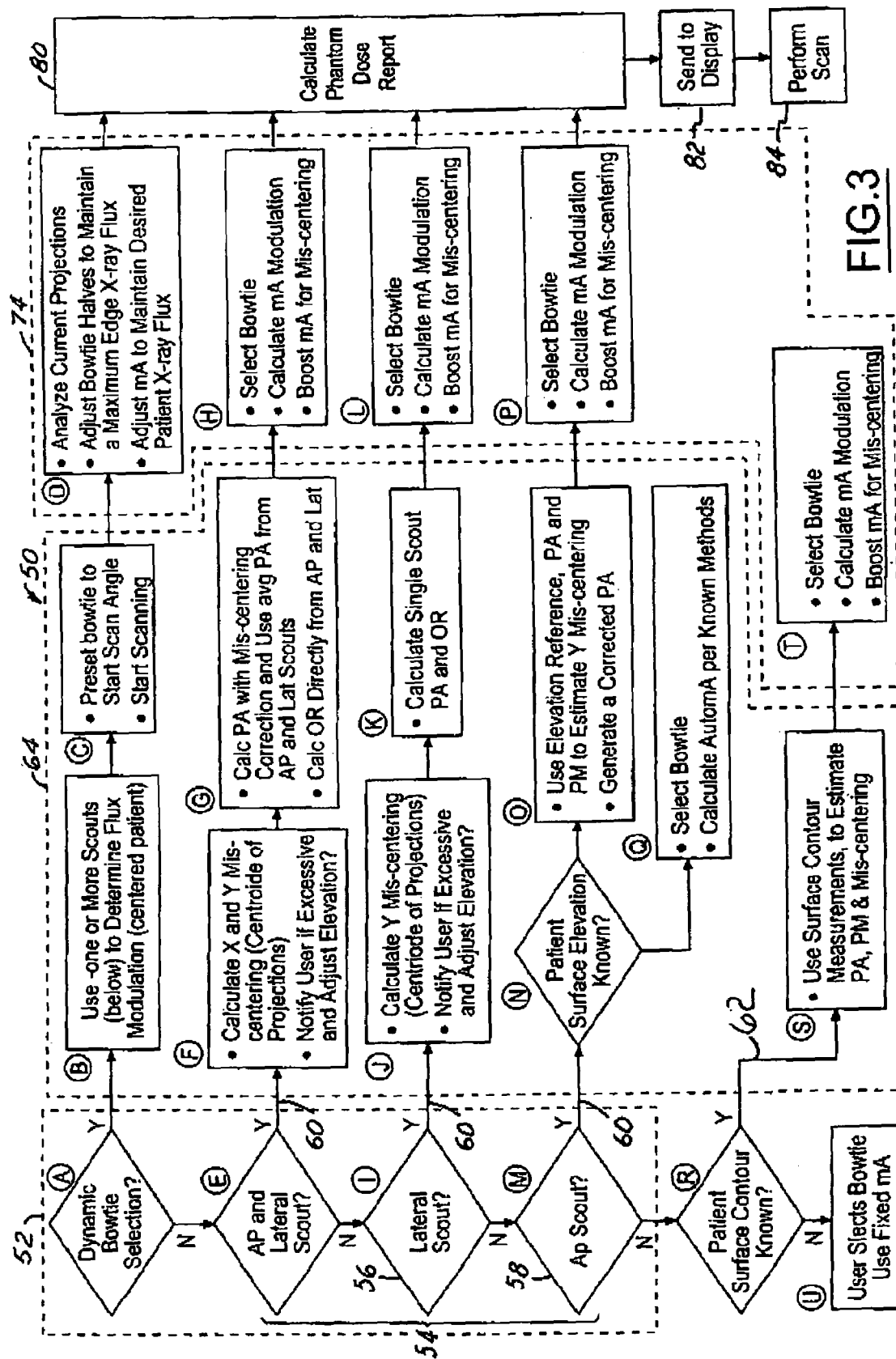
FIG. 3 is a flow chart illustration of a control mechanism for use in the computed tomography assembly illustrated in FIG. 1.

An important operational feature of the computed tomography assembly 10 is the display of computed tomography dose index volume prior to execution of the scan. This allows the operator to properly evaluate the dosage of radiation that the patient 22 will experience prior to their actually undergoing such exposure. In order to properly provide such an CTDIvol value, the present invention must first develop an accurate concept of actual patient 22 size and position. The present invention, therefore, includes within the control mechanism 26 a logic 50 adapted uniquely to provide such information. An illustration of the logic 50 is illustrated in FIG. 3. The logic 50 is adapted to execute at least one scout scan of the object/patient 52. Scout scans 54 are low intensity scans utilized to obtain positional and general information prior to full computed tomography (CT) imaging. The at least one scout scan 54 is contemplated to be comprised of lateral scout scans 56, anteroposterior scout scans 58, or multiple orthogonal scout scans. Each of the scout scans 54 produces a scout scan image 60 which in turn can be utilized to calculate an estimation of the patient size for dose calculation. It should be understood that a patient contour scan 62 may be used in conjunction or in place of the scout scans 54 for use in patient size calculation.

Figure 4:
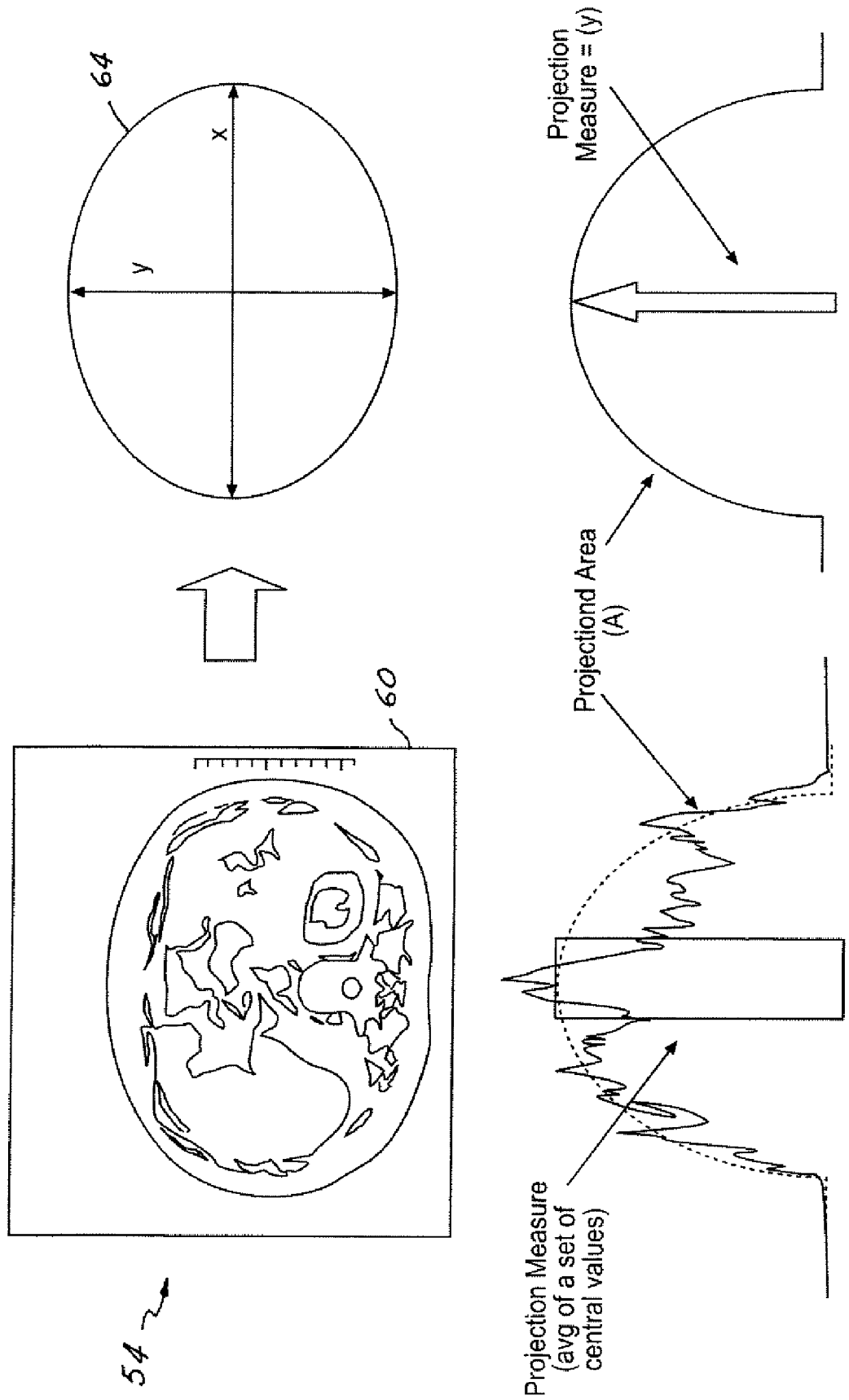
FIG. 4 is an illustration of the conversion of a scout scan image to an elliptical patient model for use in the computed tomography assembly illustrated in FIG. 1.
Figure 5:
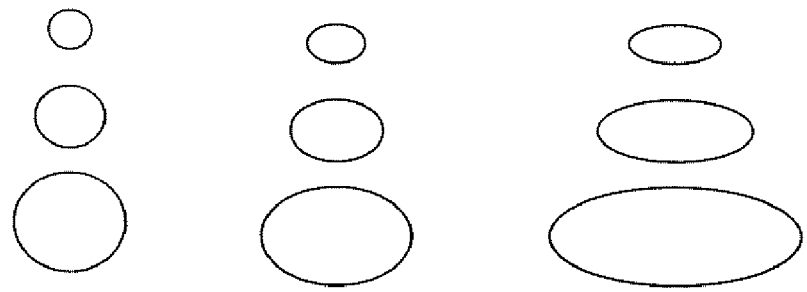
FIG. 5 is an illustration of phantom diameter approximations for use in the computed tomography assembly illustrated in FIG. 1.

The present invention provides a means to calculate the patient's 22 size, shape, and centering from the one or more scout scans 54 or patient contour scan 63. FIG. 4 illustrates the principles of using the scout scan 54 or scans to generate an elliptical patient model 64. A variety of known imaging process methods such as edge detecting are contemplated. The elliptical patient model 64 is an approximation of the patient cross-sectional area represented as an ellipse based on Projection area (PA) and amplitude (projection measure PM). Using a single scout the orthogonal projection measure (OPM) can be calculated using the formula for the area of an ellipse X=4A/PieY wherein Oval ratio=x/y. A set of phantoms (see FIG. 5) that represent the range of expected clinical sizes and shapes can be compared to the OPM such that an appropriate elliptical patient model 64 is achieved. Wherein multiple scans, or three-dimensional scans, are contemplated it should be understood that an elliptical patient model 64 is estimated for each position along the z-scanning axis. Thus the present invention can be utilized for complex scanning such as helical scanning. The present invention contemplates the estimation of the elliptical patient model 64 using a single scout scan image 60 or multiple images. The centroid of the scout scan image 60 (center of mass) can be calculated from two orthogonal scout projections. The distance of the centroid from the isocenter channel can be used to geometrically calculated the X and Y centering error for the patient 22. Use of centroid calculations Is better than edge detection methods since it yields the center of maximum attenuation that should be positioned in the maximum X-ray field rather than just the physical center relative to the edges of the object 22. Thus the scout scan images 60 can be utilized to determine not only patient 22 size but centering as well.

Figure 6:
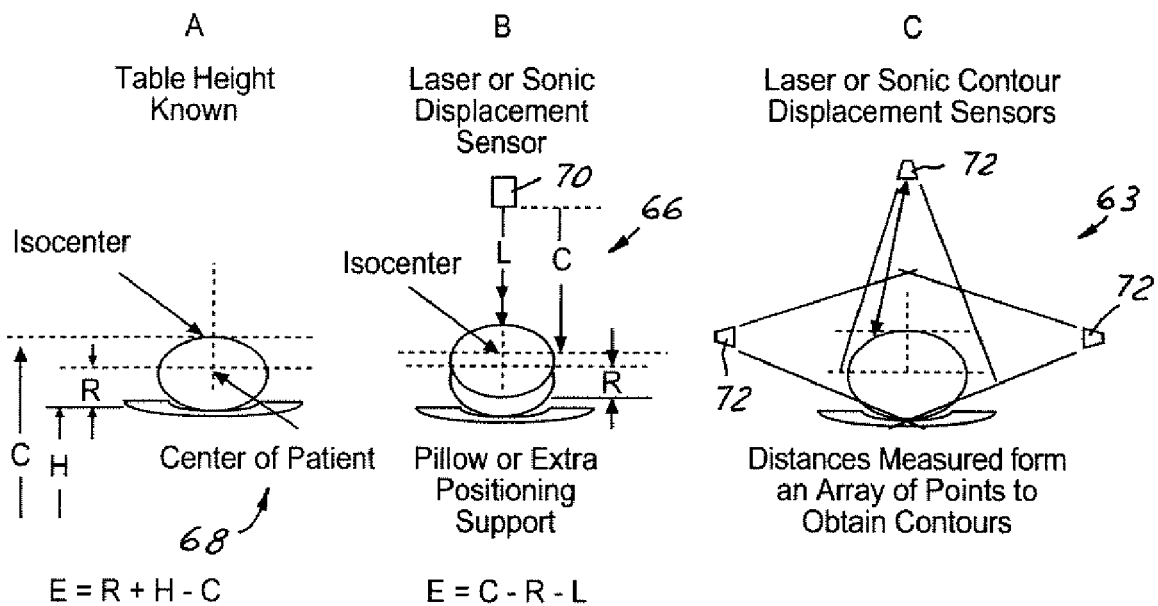
FIG. 6 is an illustration of alternate components capable of generating the patient elliptical model as described in FIG. 4.

When a single scout scan 54 is used, such as an anteroposterior scout scan 58, vertical centering errors may be difficult to calculate without knowledge of patient orientation. The present invention, therefore, utilizes surface elevation information through the use of displacement sensors 66 as shown in FIG. 6. One methodology illustrated contemplates the use of an elevation reference 68, i.e. table elevation, to determine the Y axis centering error. This estimation, however, is not accurate where the patient 22 is propped up with pillows or other positioning devices as is common. The present invention, therefore contemplates the use of laser displacement sensors 70 or sonic displacement sensors 72 to provide a vertical centering adjustment following the contours of the patient 22. Finally, a plurality of displacement sensors 70 may be utilized to measure a patients contour 72 in which case calculations utilizing the scout scans 54 can be forgone.

Figure 7:
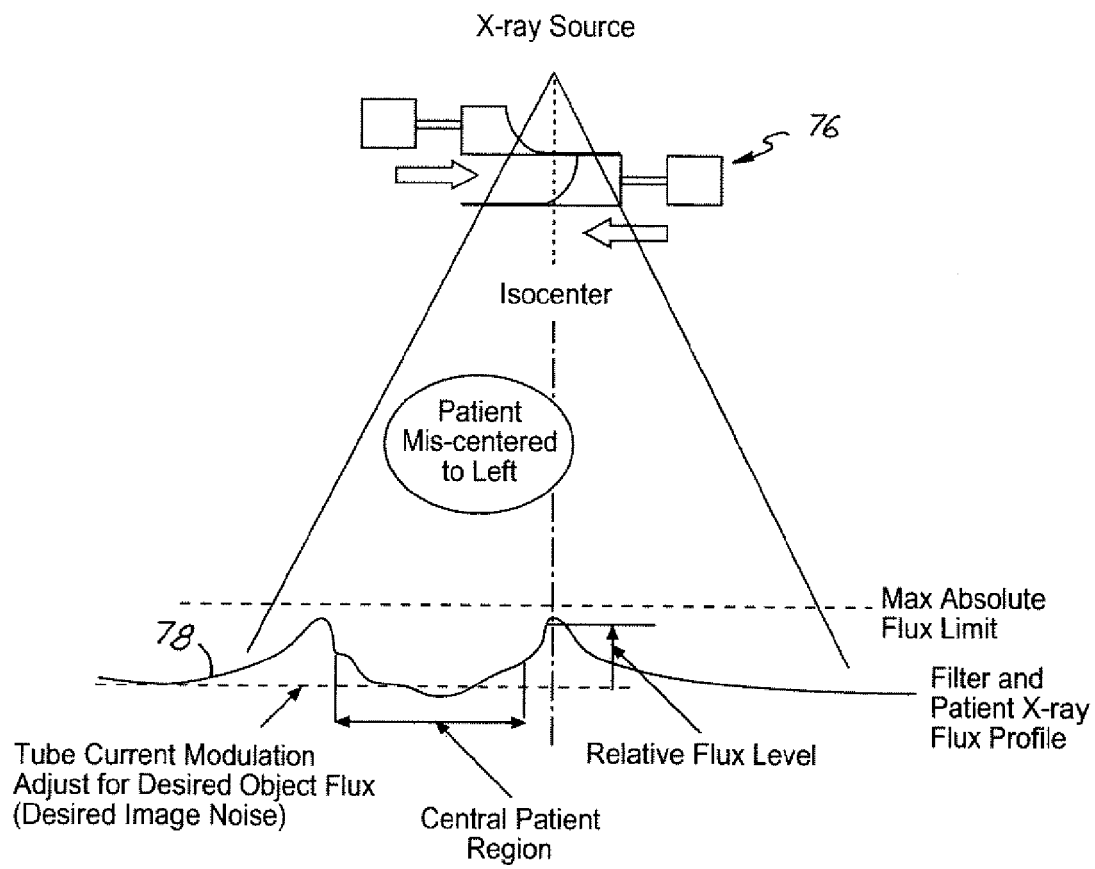
FIG. 7 is an illustration a variable bow-tie element for use by the computed tomography assembly illustrated in FIG. 1.

The present invention has therefore utilized scout scans 54 and/or other sensor scanning to generate an elliptical patient model 64 for each scanning point along the z-axis. The present invention can adjust for patient size, position, and proper centering to provide an accurate elliptical representation. The present invention further utilizes such elliptical patient models 64 in order to generate a dose minimized imaging sequence 74. This dose minimized imaging sequence 74 provides improved resolution while minimizing the dose volume received by the patient 22. In one embodiment, the present invention contemplates the dose minimized imaging sequence 74 to contemplate adjusting the size of the bowtie element 76 positioned within the x-ray source 14. This can be accomplished through substitution of bowtie elements 76 or through the use of an adjustable bowtie assembly (see FIG. 7). Furthermore, the current modulation 78 of the x-ray source 14 may be adjusted on the basis of the elliptical patient model 64. The bowtie 76 and current modulation 78 may also be used to compensate for misscentering of the patient 22 in relation to the x-ray source.

Figure 8:
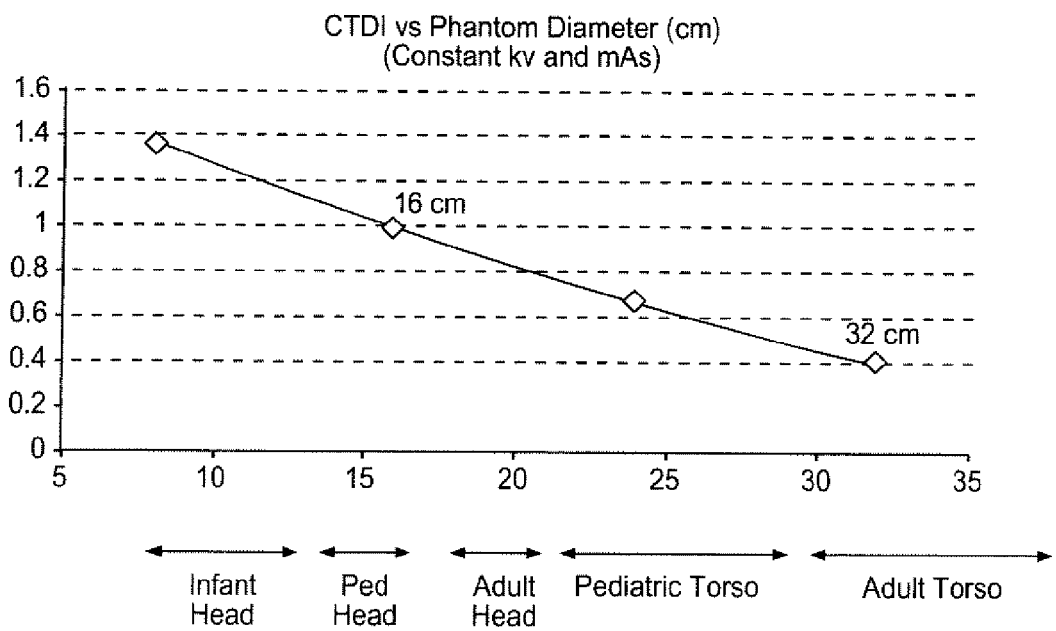
FIG. 8 is an illustration of a database of CTDIvol to phantom diameter approximations for use in the computed tomography assembly illustrated in FIG. 1.

While an imaging sequence 74 that minimizes radiation exposure to the patient 22 is calculated, the present invention contemplates a proper calculation of the CTDIvol 80 and communication of this dose volume to the display 82 prior to actual implementation of the imaging 84. The present invention does this by comparing the patient elliptical model 64 to one of the phantom diameter approximations 86 (see FIG. 5). The phantom diameter approximation 86 closes to the patient elliptical model 64 is chosen. Phantoms represent known physical devices placed within the CT assembly 10 that measure dosage for given exposure settings (imaging sequences). Databases of phantom size versus CTDI, for constant kv and mAs, can be included such that specific dosage volumes can be calculated for a given phantom size and a given current (FIG. 8). Although a variety of sizes of phantoms may be generated, the two standard sizes for CTDI are 16 cm and 32 cm phantoms. The present invention, therefore, generated a dose report based on the phantom diameter approximation 86 selected in comparison to the dose minimized imaging sequence 74. By varying both the dose minimized imaging sequence 74 and the phantom diameter approximation 86 for each imaging slice along a patient 22, the present invention allows for a far more reliable and accurate dosage report than existing methodologies.

While particular embodiments of the invention have been shown and described, numerous variations and alternative embodiments will occur to those skilled in the art. Accordingly, it is intended that the invention be limited only in terms of the appended claims.

The invention claim is:

1. A computed tomography assembly comprising:
an x-ray gantry assembly;
an x-ray source projecting a beam of x-rays;
a detector assembly positioned opposite said x-ray source, said detector assembly receiving said beam of x-rays after said beam of x-rays pass through an object;
a control mechanism in communication with said x-ray source and said detector assembly;
an elevation reference in communication with said control mechanism, said control mechanism comprising logic adapted to:
execute at least one scout scan of said object, said at least one scout scan producing a first scout scan image;
generate an elliptical patient model based on said first scout scan image;
match said elliptical patient model to a phantom diameter approximation;
generate a dose report based on said phantom diameter approximation;
display said dose report on a display, said display in communication with said control mechanism; and
utilize said elevation reference in combination with said at least one scout scan to generate said elliptical patient model.

2. A computed tomography assembly as described in claim 1, wherein said at least one scout scan comprises two orthogonal scout scans.

3. A computed tomography assembly as described in claim 1, wherein said at least one scout scan comprises:
a lateral scout scan; and
an anteroposterior scout scan.

4. A computed tomography assembly as described in claim 1, wherein said logic is adapted to further comprise:
utilizing said elliptical patient model to generate a dose minimized imaging sequence.

5. A computed tomography assembly as described in claim 4, wherein said dose report is generated by combining said phantom diameter approximation with said dose minimized imaging sequence.

6. A computed tomography assembly as described in claim 4, wherein dose minimized imaging sequence comprises:
adjusting a bowtie element positioned within said x-ray source to minimize radiation exposure to said object.

7. A computed tomography assembly as described in claim 4, wherein dose minimized imaging sequence comprises:
adjusting a current modulation of said x-ray source to minimize radiation exposure to said object.

8. A computed tomography assembly as described in claim 4, wherein dose minimized imaging sequence comprises:
calculating object centering information;
adjusting a current modulation of said x-ray source to compensate for said object centering information.

9. A computed tomography assembly as described in claim 4, wherein dose minimized imaging sequence comprises:
calculating object centering information;
adjusting a bowtie element positioned within said x-ray source to compensate for said object centering information.

10. A computed tomography assembly comprising:
an x-ray gantry assembly;
an x-ray source projecting a beam of x-rays;
a detector assembly positioned opposite said x-ray source, said detector assembly receiving said beam of x-rays after said beam of x-rays pass through an object;
a control mechanism in communication with said x-ray source and said detector assembly;
at least one laser position measurement device in communication with said control mechanism said control mechanism comprising logic adapted to:
execute at least one scout scan of said object, said at least one scout scan producing a first scout scan image;
utilize said laser position measurement device in combination with said at least one scout scan to generate said elliptical patient model;
match said elliptical patient model to a phantom diameter approximation;
generate a dose report based on said phantom diameter approximation; and
display said dose report on a display, said display in communication with said control mechanism.

11. A computed tomography assembly comprising:
an x-ray gantry assembly;
an x-ray source projecting a beam of x-rays;
a detector assembly positioned opposite said x-ray source, said detector assembly receiving said beam of x-rays after said beam of x-rays pass through an object;
a control mechanism in communication with said x-ray source and said detector assembly;
at least one sonic displacement device in communication with said control mechanism, said control mechanism comprising logic adapted to:
execute at least one scout scan of said object, said at least one scout scan producing a first scout scan image;
utilize said sonic displacement device in combination with said at least one scout scan to generate said elliptical patient model; and
match said elliptical patient model to a phantom diameter approximation;

generate a dose report based on said phantom diameter approximation; and display said dose report on a display, said display in communication with said control mechanism.

12. A computed tomography assembly comprising:
an x-ray gantry assembly;
an x-ray source projecting a beam of x-rays;
a detector assembly positioned opposite said x-ray source, said detector assembly receiving said beam of x-rays after said beam of x-rays pass through an object;
a control mechanism in communication with said x-ray source and said detector assembly, said control mechanism comprising logic adapted to:
execute at least one scan of said object, said at least one scan producing a first scan image;
generate an elliptical patient model based on said first scan image;
match said elliptical patient model to a phantom diameter approximation;
generate a dose report based on said phantom diameter approximation;
display said dose report on a display, said display in communication with said control mechanism; and
utilize said elliptical patient model to generate a dose minimized imaging sequence;
wherein dose minimized imaging sequence comprises:
calculating object centering information;
adjusting a current modulation of said x-ray source to compensate for said object centering information.

13. A computed tomography assembly as described in claim 12, wherein said dose report is generated by combining said phantom diameter approximation with said dose minimized imaging sequence.

14. A computed tomography assembly as described in claim 12, wherein dose minimized imaging sequence comprises:
adjusting a bowtie element positioned within said x-ray source to minimize radiation exposure to said object.

15. A computed tomography assembly as described in claim 12, wherein dose minimized imaging sequence comprises:
adjusting a current modulation of said x-ray source to minimize radiation exposure to said object.

16. A computed tomography assembly as described in claim 12, wherein said at least one scan comprises two orthogonal scout scans.

17. A computed tomography assembly as described in claim 12, wherein said at least one scan comprises a contour displacement sensor scan.

18. A method of imaging an object utilizing a computed tomography assembly comprising:
executing at least one scout scan of the object, said at least one scout scan producing a first scout scan image;
utilizing an elevation reference in combination with said at least one scout scan to generate an elliptical patient model using a control mechanism;
matching said elliptical patient model to a phantom diameter approximation using said control mechanism;
generating a dose report automatically based on said phantom diameter approximation; and
display said dose report on a display, said display in communication with said control mechanism.

* * * * *